Sept. 17, 1940. W. KORDES Plant Pat. 423
ROSE PLANT
Filed May 23, 1940
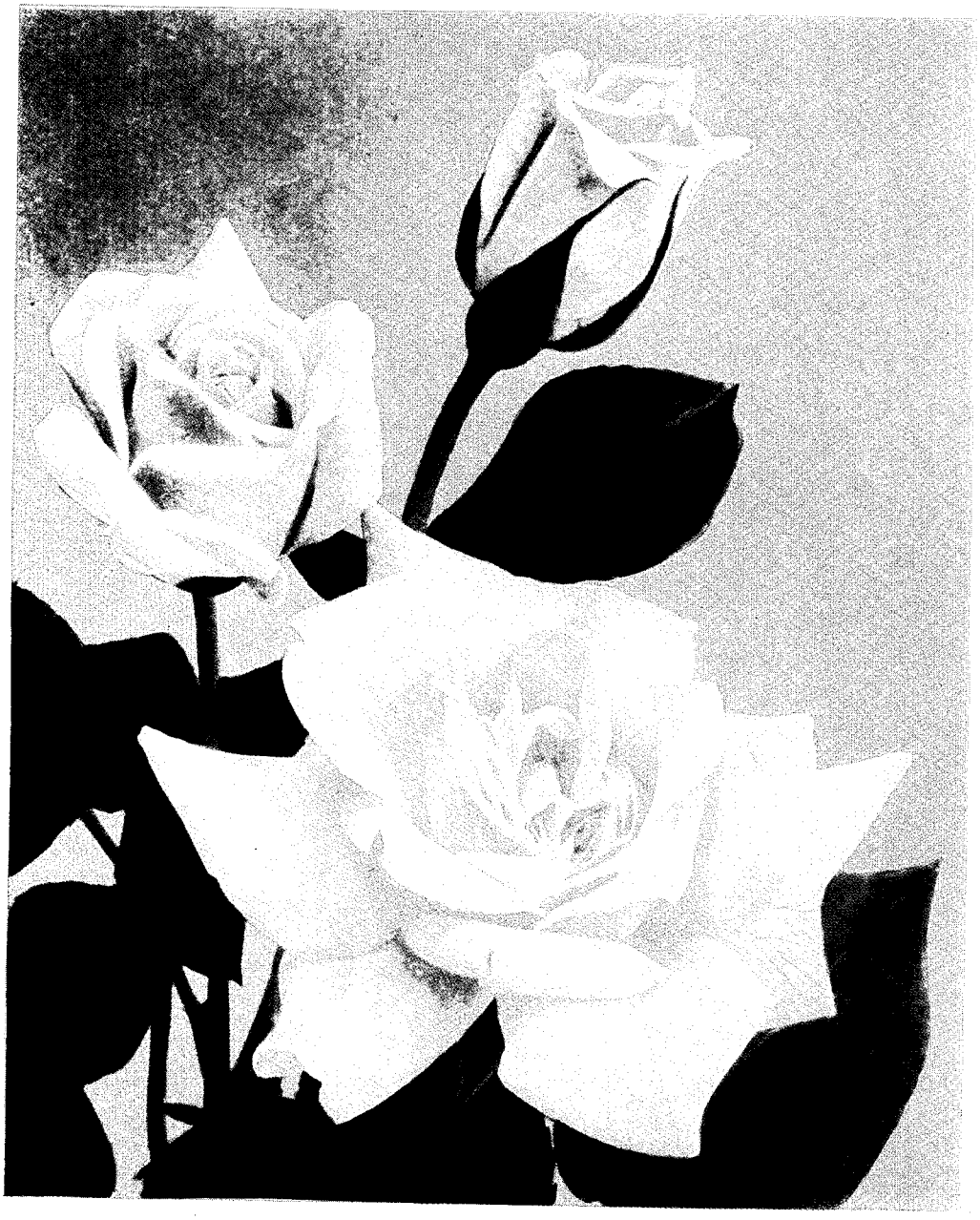
Inventor
Wilhelm Kordes
By Robert Robb
Attorney Patented Sept. 17, 1940 Plant Pat. 423

UNITED STATES PATENT OFFICE

423

ROSE PLANT

Wilhelm Kordes, Sparrieshoop in Holstein, Germany, assignor to Jackson & Perkins Company, Newark, N. Y.

Application May 23, 1940, Serial No. 336,872

1 Claim. (Cl. 47—61)

The present invention relates to a new and distinct variety of Rose plant, resulting from a cross between "Joanna Hill" x "Etoile d'Or."

This new rose grown from a seedling of the above mentioned cross is quite distinctive from either of its parents or other roses in its class, and is characterized as to novelty by its upright growth and its Dark Cress Green top and reverse Turtle Green foliage; also by the coloring of its flower, running from Peach Red petals when the sepals first divide, developing in the bud to Orange Buff when the petals begin to unfurl, to the Capucine Yellow of the outer petals, and Capucine Orange in the center of the open flower. It is further notable for the Capucine Yellow veinations extending to the top of the reverse of the petals of the open flower.

The foregoing distinctions are more specifically referred to in the following detailed description, wherein all color terminology accords with the Ridgway Color Standard:

Parentage:
*Seedling*—
Seed parent—Joanna Hill.
Pollen parent—Etoile d'Or.
Classification:
Botanic and commercial—Hybrid Tea.

*Flower*

Blooming habit:
(Observations made in fields and gardens of Jackson & Perkins Company, Newark, New York, in the morning of September 6, 1939.)
Blooms once—Profusely.
Recurrent—Continuous.
Bud:
*Size*—Medium.
*Form*—Long, pointed. Is not affected by wet or hot weather.
*Color:*
When sepals first divide—Peach Red, Plate 1.
When petals begin to unfurl—Orange Buff, Plate 3.
When half blown—
Inside of petals—Between Orange Buff, Plate 3, and Light Orange Yellow, Plate 3.
Reverse of petals — Mikado Orange, Plate 3.
*Sepals*—Branched.
Curl back when flower opens fully.
*Calyx*—
Shape—Funnel.
Size—Small.
Aspect—Smooth.
Odor when rubbed—None.
*Peduncle*—
Length—Medium.
Aspect—Smooth.
Color—Cosse Green, Plate 5.
Strength—Erect, slender.
*Opening:*
Bud opens well. Is not affected by adverse conditions.
Bloom:
*Size*—Large. Average size when fully expanded—4-4½ inches.
*Borne*—Singly.
*Stems*—Medium length; strong.
*Form:*
When first open—High center.
Permanence—Retains its form to the end.
*Petalage*—Double (full but open center). Number of petals under normal conditions—55.
*Color:*
Center of flower—Capucine Orange, Plate 3.
Outer petals—Capucine Yellow, Plate 3.
Base of petals (aiglet)—Empire Yellow, Plate 4.
Inside of petals—Apricot Yellow, Plate 4, shading to Lemon Chrome, Plate 4, near the bottom.
Reverse of petals—Salmon Orange, Plate 2.
General tonality from a distance—Capucine Orange, Plate 2, to Apricot Yellow Plate 4.
*Variegations*—Veined, reverse of petals with Capucine Orange, Plate 2, through to the top of the petal.
*Discoloration*—
General tonality at the end of the first day—Capucine Orange, Plate 3, to Apricot Yellow, Plate 4.
Second day—Apricot Yellow, Plate 4.
Third day—Buff Yellow, Plate 4, and edges slightly tinged with Orient Pink, Plate 2.
Petals:
*Texture*—Thick, soft. Is not affected by wet weather, or hot weather.
*Appearance*—
Inside and outside—Satiny.
*Form*—Oval.
*Arrangement*—Informal (with "rags" in center slightly quartered). Petaloids in center—Few, small.

*Pesistence*—Drop off cleanly.
*Fragrance*—Moderate.
Nature—Tea (average Hybrid Tea scent).
*Lasting quality*—On the plant and as cut flower—Long.
Genital organs:
*Stamens, anthers*—
Size—Medium; many.
Color—Light Cadmium, Plate 4.
Arrangement—Regular around styles.
*Stamens, filaments (threads)*—Short.
Color—Bittersweet Pink, Plate 2.
*Pollen*—Empire Yellow, Plate 4.
*Styles*—Bunched; uneven length; medium length; thin.
*Stigmas*—Baryta Yellow, Plate 4.
*Ovaries*—All enclosed in calyx.

*Plant*

Form:
Bush.
Growth:
Vigorous, upright.
Foliage:
5 leaflets.
*Size*—Medium.
*Quantity*—Normal.
*Color:*
New foliage—
*Upper side*—Ray's Russet, Plate 14, over Kronberg's Green, Plate 31.
*Under side*—Rainette Green, Plate 31, with cast of Vinaceous Russet, Plate 28.
Old foliage—
*Upper side*—Dark Cress Green, Plate 31.
*Under side*—Light Turtle Green, Plate 32.
Shape—Oval pointed.
Texture—
*Upper side*—Leathery.
*Under side*—Smooth; ribs and veins—prominent.
Edge—Serrated (saw toothed).
Serration—Single; small, sharp.
Rachis—
Color—Light Turtle Green, Plate 32.
Under side—Prickles.
Stipules—Short; serrated, bearded.
Disease resistance—Resistant.
Wood:
*New wood*—Rainette Green, Plate 31, with cast of Vinaceous Russet, Plate 28.
Bark—Smooth.
*Old wood*—
Color—Cress Green, Plate 31.
Bark—Smooth.
Thorns: (Divided into thorns, prickles and short needles).
*Thorns*—
Quantity—
On main stalks from base—Few.
On laterals from stalk—Few.
Form — Broad base; medium length, straight.
Color when young—Honey Yellow, Plate 30.
Position—Irregular.
*Prickles*—
Quantity—
On main stalks—Few.
On laterals—None.

Asexual reproduction of this new rose shows that the noted distinctive features are fixed.

I claim:

A new and distinct variety of Rose plant, characterized as to novelty by its upright habit of growth, the coloring of its foliage, and the attractive coloring of the petals of the flower in the different stages of development, substantially as shown and described.

WILHELM KORDES.